Figure 1:
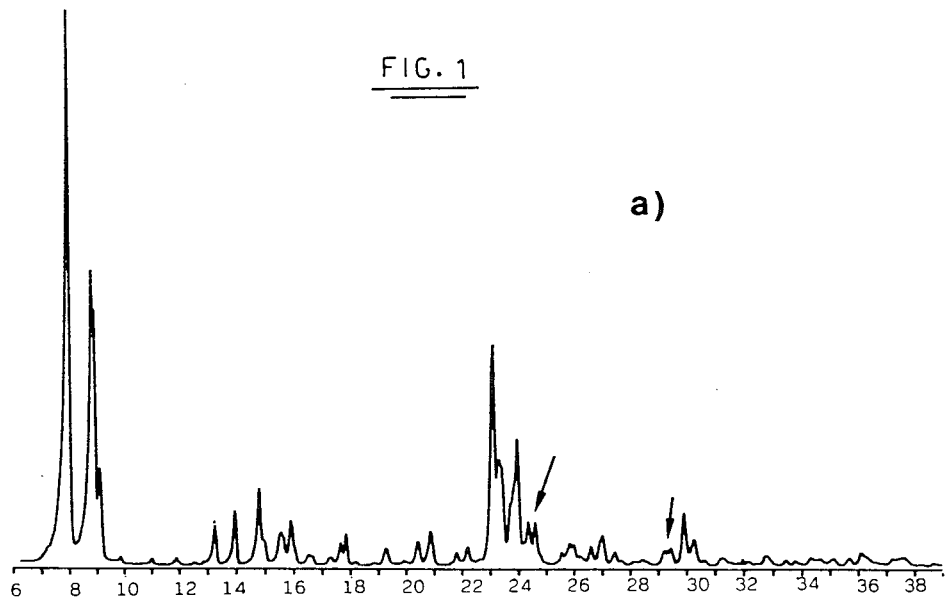
Figure 1:
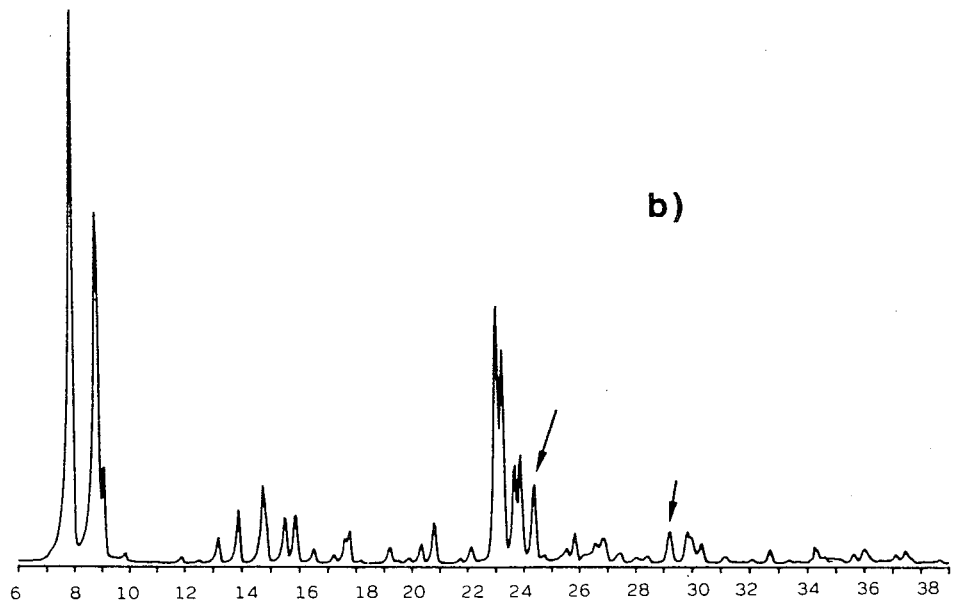

United States Patent [19]

Neri et al.

[11] Patent Number: 4,609,765
[45] Date of Patent: Sep. 2, 1986

[54] PROCESS FOR OXIDIZING VINYLBENZENE COMPOUNDS TO β-PHENYLALDEHYDES

[75] Inventors: Carlo Neri; Franco Buonomo, both of S.Donato Milanese, Italy

[73] Assignee: Anic, S.p.A., Palermo, Italy

[21] Appl. No.: 513,804

[22] Filed: Jul. 14, 1983

[30] Foreign Application Priority Data

Jul. 28, 1982 [IT] Italy .............................. 22610 A/82

[51] Int. Cl.⁴ .............................................. C07C 45/27
[52] U.S. Cl. ..................................................... 568/430
[58] Field of Search ......................................... 568/430

[56] References Cited

U.S. PATENT DOCUMENTS 2,414,385  1/1947  Milas ................................... 568/430

*Primary Examiner*—Bernard Helfin
*Attorney, Agent, or Firm*—Hedman, Gibson, Costigan & Hoare

[57] ABSTRACT

A process for oxidizing vinylbenzene compounds, consisting of reacting said compounds with an aqueous solution of hydrogen peroxide in the presence of synthetic zeolites containing titanium atoms, of general formula:

$$xTiO_2.(1-x)SiO_2$$

where x lies between 0.0001 and 0.04, and possibly in the presence of one or more solvents, operating at a temperature of between 20° and 150° C.

12 Claims, 2 Drawing Figures

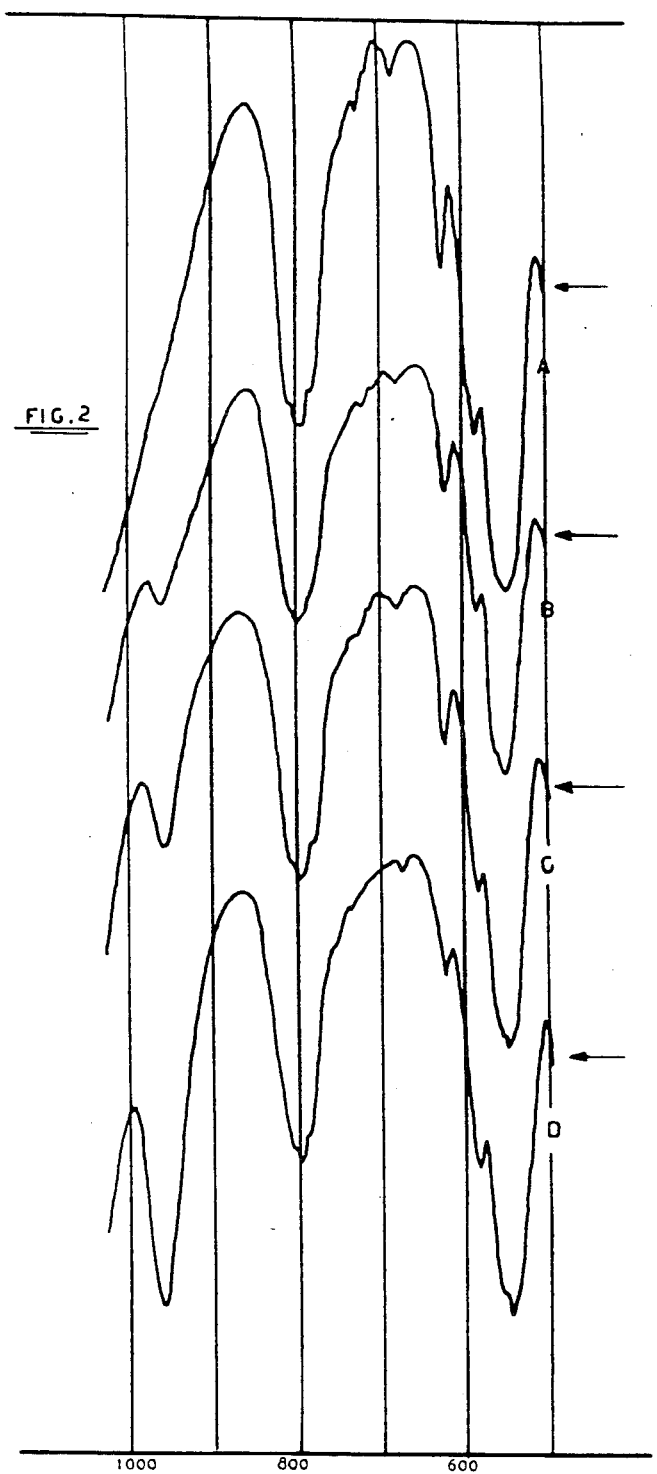

PROCESS FOR OXIDIZING VINYLBENZENE COMPOUNDS TO β-PHENYLALDEHYDES

This invention relates to a process for oxidising vinylbenzene compounds to β-phenylaldehydes by hydrogen peroxide in the presence of synthetic zeolites containing titanium atoms.

It is known to obtain β-phenylaldehydes from vinylbenzene oxides in the presence of alumino-silicates, by operating at high temperature. For example, β-phenylacetaldehyde is produced from styrene oxide in the presence of alumino-silicates, the reaction being conducted at a temperature of about 300° C.

It has now been surprisingly found possible to produce β-phenylaldehydes by using hydrogen peroxide in aqueous solution to oxidise vinylbenzene compounds, employing as catalyst a synthetic zeolite containing titanium atoms, and at the same time attaining considerable economic advantage.

These economic advantages derive both from the use of a vinylbenzene compound instead of its oxide, which is notably more costly, and from operating at a substantially lower reaction temperature. The subject matter of the present invention is a process for oxidising vinylbenzene compounds to β-phenylaldehydes, consisting of reacting said compounds with an aqueous solution of hydrogen peroxide in the presence of synthetic zeolites containing titanium atoms (titanium silicalites), of the following general formula:

$$xTiO_2 \cdot (1-x)SiO_2,$$

where x lies between 0.0001 and 0.04, and possibly in the presence of one or more solvents.

The synthetic zeolites used for the oxidation reaction are described in Belgian Pat. No. 886,812, of which we repeat some points illustrating the material and relative method of preparation. The composition range of the titanium silicalite expressed in terms of molar ratios of the reagents is as follows:

| Molar ratio of reagents | | preferably |
| --- | --- | --- |
| $SiO_2/TiO_2$ | 5–200 | 35–65 |
| $OH^-/SiO_2$ | 0.1–1.0 | 0.3–0.6 |
| $H_2O/SiO_2$ | 20–200 | 60–100 |
| $Me/SiO_2$ | 0.0–0.5 | 0 |
| $RN^+/SiO_2$ | 0.1–2.0 | 0.4–1.0 |

$RN^+$ indicates the nitrogenated organic cation deriving from the organic base used for the preparation of the titanium silicalite (TS-1).

Me is an alkaline ion, preferably Na or K.

The final TS-1 has a composition satisfying the formula $xTiO_2 \cdot (1-x)SiO_2$, where x lies between 0.0001 and 0.04, and preferably between 0.01 and 0.25. The TS-1 is of the silicalite type, and all the titanium substitutes the silicon.

The synthetic material has characteristics which are shown up by X-ray and infrared examination.

The X-ray examination is carried out by means of a powder diffractometer provided with an electronic pulse counting system, using the radiation $CuK\alpha^-$. The titanium silicalites (TS-1) are characterised by a X-ray diffraction spectrum as shown in FIG. 1b. This spectrum is similar overall to the typical spectrum of silicalite (FIG. 1a), however it has certain clearly "single" reflections where double reflections are evident in the pure silicalite spectrum.

Because the spectral differences between TS-1 and silicalite are relatively small, special accuracy is required in the spectral determination. For this reason TS-1 and silicalite were examined by the same apparatus, using $Al_2O_3$ as the internal standard. Table 1 shows the most significant spectral data of a TS-1 where x=0.017, and of a pure silicalite.

The constants of the elementary crystalline cell were determined by the minimum square method, on the basis of the interplanar distances of 7–8 single reflections lying within the range of 10°–40° $2\theta$.

A large proportion of the interplanar distances of TS-1 are tendentially greater than the corresponding distances of pure silicalite, although only slightly, which is in accordance with the larger predictable value of the Ti—O bond distance relative to that of the Si—O bond distance.

Passage from a double reflection to a single reflection is interpreted as a change from a monoclinic symmetry (pseudo orthorhombic) (silicalite) to an effective orthorhombic symmetry, "titanium silicalite" (TS-1). In FIG. 1, the most apparent aforesaid spectral differences are indicated by arrows.

INFRARED EXAMINATION

TS-1 shows a characteristic absorption band at about 950 cm$^{-1}$ (see FIG. 2, spectra B, C and D) which is not present in the pure silicalite spectrum (FIG. 2, spectrum A), and is also absent in titanium oxides (rutile, anastase) and in alkaline titanates.

Spectrum B is that of TS-1 with 5 mol% of $TiO_2$, spectrum C is that of TS-1 with 8 mol% of $TiO_2$, and spectrum D is that of TS-1 with 2.3 mol% of $TiO_2$.

As can be seen from FIG. 2, the band intensity at approximately 950 cm$^{-1}$ increases with the quantity of titanium which substitutes the silicon in the silicalite structure.

MORPHOLOGY

From a morphological aspect, TS-1 is in the form of parallelepipeds with chamfered edges. A X-ray microprobe examination has shown that the titanium distribution within the crystal is perfectly uniform, thus confirming that the titanium substitutes the silicon in the silicalite structure, and is not present in other forms.

The process for preparing titanium silicalite comprises the preparation of a reaction mixture consisting of sources of silicon oxide, titanium oxide and possibly an alkaline oxide, a nitrogenated organic base and water, the composition in terms of the molar reagent ratios being as heretofore defined.

The silicon oxide source can be a tetraalkylorthosilicate, preferably tetraethylorthosilicate, or simply a silicate in colloidal form, or again a silicate of an alkaline metal, preferably Na or K. The titanium oxide source is a hydrolysable titanium compound preferably chosen from TiCl$_4$, TiOCl$_2$ Ti(alkoxy)$_4$, preferably Ti(OC$_2$H$_5$)$_4$.

The organic base is tetraalkylammonium hydroxide, and in particular tetrapropylammonium hydroxide.

The reagent mixture is subjected to hydrothermal treatment in an autoclave at a temperature of between 130° and 200° C. under its own developed pressure, for a time of 6–30 days until the crystals of the TS-1 precursor are formed. These are separated from the mother solution, carefully washed with water and dried. When in the anhydrous state they have the following composition:

The precursor crystals are heated for between 1 and 72 hours in air at 550° C. to completely eliminate the nitrogenated organic base. The final TS-1 has the following composition:

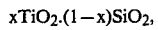

where x is as heretofore defined. Chemical and physical examinations are carried out on the products thus obtained.

The vinylbenzene compounds which can be oxidised in accordance with the invention satisfy the general formula:

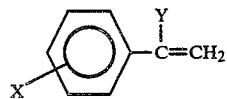

where X is H, CH$_3$ or OCH$_3$, and Y is H or CH$_3$.

Said vinylbenzene compounds give the corresponding β-phenylaldehydes:

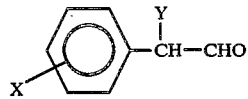

where X and Y are as heretofore specified.

The products obtained in this manner can be used as such in the pharmaceutical field or in perfumery, or can be reduced to alcohols or further oxidised to acids.

For example, β-phenylacetaldehyde can be reduced by any known method to β-phenylethylalcohol (which is widely used in perfumery) or oxidised to phenylacetic acid (which is widely used in the pharmaceutical field).

The reactions between vinylbenzene compounds and hydrogen peroxide are carried out at a temperature of between 20° and 150° C., and preferably between 50° and 100° C., under the self-generated pressure deriving from the vapour pressure of the solvent or hydrocarbon at the reaction temperature.

Moreover, the reactions can be carried out with H$_2$O$_2$ in aqueous solution, even at low concentration, from 10 to 70% w/v.

The solvent used can be any polar compound such as alcohols, ketones, ethers, glycols or acids, with a number of carbon atoms which is not too high and is preferably less than or equal to 6. Methanol or tert.butanol is the most preferred of the alcohols, and acetone the most preferred of the ketones.

The reaction system is biphase if solvent is absent, whereas it is monophase in the presence of any solvent able to render the system homogeneous.

The manner of operating the process according to the present invention and its advantages will be more apparent from an examination of the following illustrative examples, which however in no way limit the invention.

EXAMPLES 1–16

40 cc of solvent, 20 cc of hydrocarbon, 7.5 cc of 36% w/v H$_2$O$_2$ and 2.5 g of titanium silicalite are fed into a 250 cc glass autoclave.

The autoclave is immersed under magnetic stirring in a bath temperature-controlled at the required temperature, and the disappearance of the H$_2$O$_2$ is followed with time by withdrawing small samples of solution.

When the reaction is complete, the solution is analysed by G.L.C. The results are indicated in Table 2, in which the H$_2$O$_2$ yield indicates the ratio of the moles of styrene transformed to the moles of H$_2$O$_2$ reacted, the aldehyde selectivity signifies the ratio of the moles of aldehyde formed to the moles of styrene transformed, and the styrene selectivity signifies the ratio of the moles of styrene which have formed oxidation products to the moles of styrene transformed.

The oxidation products other than aldehyde are:
in methanol: glycol monomethylether (1-methoxy-2-phenylethanol)
in acetone: styrene glycol and its ketal
in tert.butanol and in H$_2$O: glycol.

TABLE 1

| | TS - 1 | | | Silicalite[a] | | |
|---|---|---|---|---|---|---|
| 2θ' (Cukα) | Inter-planar distance d(Å) | Rel. Int.[b] | | 2θ' (Cukα) | Inter-planar distance d(Å) | Rel. Int.[b] |
| 7.94 | 11.14 | vs | | 7.94 | 11.14 | vs |
| 8.85 | 9.99 | s | | 8.85 | 9.99 | s |
| 9.08 | 9.74 | m | | 9.08 | 9.74 | m |
| 13.21 | 6.702 | w | | 13.24 | 6.687 | w |
| 13.92 | 6.362 | mw | | 13.95 | 6.348 | mw |
| 14.78 | 5.993 | mw | | 14.78 | 5.993 | mw |
| 15.55 | 5.698 | w | | 15.55 | 5.698 | w* |
| 15.90 | 5.574 | w | | 15.90 | 5.574 | w |
| 17.65 | 5.025 | w | | 17.65 | 5.025 | w |
| 17.81 | 4.980 | w | | 17.83 | 4.975 | w |
| 20.37 | 4.360 | w | | 20.39 | 4.355 | w |
| 20.85 | 4.260 | mw | | 20.87 | 4.256 | mw |
| 23.07 | 3.855 | s | | 23.08 | 3.853 | s |
| | | | | 23.28 | 3.821 | ms |
| 23.29 | 3.819 | s | | | | |
| | | | | 23.37 | 3.806 | ms |
| | | | | 23.71 | 3.753 | ms |
| 23.72 | 3.751 | s | | | | |
| | | | | 23.80 | 3.739 | ms |
| 23.92 | 3.720 | s | | 23.94 | 3.717 | s |
| | | | | 24.35 | 3.655 | mw |
| 24.41 | 3.646 | m | | | | |
| | | | | 24.60 | 3.619 | mw |
| | | | | 25.84 | 3.448 | w |
| 25.87 | 3.444 | w | | | | |
| | | | | 25.97 | 3.431 | w |
| 26.87 | 3.318 | w* | | 26.95 | 3.308 | w* |
| | | | | 29.23 | 3.055 | w |
| 29.27 | 3.051 | mw | | | | |
| | | | | 29.45 | 3.033 | w |
| 29.90 | 2.988 | mw | | 29.90 | 2.988 | mw |
| 30.34 | 2.946 | w | | 30.25 | 2.954 | w |

TABLE 1-continued

| | TS - 1 | | | Silicalite[a] | |
|---|---|---|---|---|---|
| $2\theta'$ (Cuk$\bar{\alpha}$) | Inter-planar distance d(Å) | Rel. Int.[b] | $2\theta'$ (Cuk$\bar{\alpha}$) | Inter-planar distance d(Å) | Rel. Int.[b] |
| 45.00 | 2.014 | mw* | 45.05 | 2.012 | mw* |
| 45.49 | 1.994 | mw* | 45.60 | 1.989 | mw* |

[a]Prepared by the method of U.S. Pat. No. 4,061,724; product calcined at 550° C.
[b]vs: very strong; s: strong; ms: medium-strong; m: medium; mw: medium-weak; w: weak; *: multiplet.

TABLE 2

| EX. N° | HYDROCARBON | SOLVENT | T °C. | t hours | $H_2O_2$ YIELD % | ALDEHYDE SELECTIVITY % | STYRENE SELECTIVITY % |
|---|---|---|---|---|---|---|---|
| 1 | STYRENE | METHANOL | 80 | 0.5 | 87 | 75.5 | 93 |
| 2 | " | ACETONE | 90 | 1 | 80 | 85.3 | 90 |
| 3 | " | t-BUTANOL | 90 | 1 | 83 | 87.3 | 92 |
| 4 | " | —($H_2O$) | 85 | 1.5 | 85 | 72.8 | 91.5 |
| 5 | METHYL STYRENE | METHANOL | 85 | 0.5 | 75 | 68.3 | 86.5 |
| 6 | " | ACETONE | 90 | 1 | 73 | 72 | 88 |
| 7 | " | t-BUTANOL | 100 | 0.5 | 78 | 74.6 | 87.2 |
| 8 | " | —($H_2O$) | 90 | 1.2 | 78 | 71.3 | 89.6 |
| 9 | 4-METHYL STYRENE | METHANOL | 85 | 0.5 | 92 | 82 | 91.6 |
| 10 | " | ACETONE | 85 | 0.5 | 90 | 82 | 88.7 |
| 11 | " | t-BUTANOL | 90 | 1 | 91.5 | 80.3 | 90 |
| 12 | " | —($H_2O$) | 100 | 1 | 90 | 85 | 92.3 |
| 13 | 4-METHOXY STYRENE | METHANOL | 80 | 0.4 | 94.5 | 90 | 94.7 |
| 14 | " | ACETONE | 80 | 0.6 | 93 | 88.7 | 91.8 |
| 15 | " | t-BUTANOL | 90 | 1 | 91.6 | 90.2 | 89.7 |
| 16 | " | —($H_2O$) | 95 | 1 | 95 | 86.8 | 87.3 |

We claim:

1. A process for oxidizing vinylbenzene compounds having the formula:

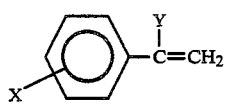

wherein X is H, $CH_3$ or $—OCH_3$; Y is H or $CH_3$ to beta-phenylaldehydes wherein said compounds are reacted with aqueous hydrogen peroxide at at temperature of 20°–150° C. in the presence of a catalyst which consists essentially of titanium silicalite that contains titanium and silicon wherein the ratio of titanium, taken as the oxide, to silicon, taken as the oxide is defined by the formula:

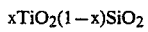

wherin x is between 0.0001 and 0.04.

2. A process as claimed in claim 1, characterized in that the oxidation reaction is conducted at a temperature of between 50° and 100° C.

3. A process as claimed in claim 1, characterised in that the oxidation reaction is conducted under self-generated pressure.

4. A process as claimed in claim 1, wherein the hydrogen peroxide is in dilute aqueous solution.

5. A process as claimed in claim 1, wherein the hydrogen peroxide in the aqueous solution is between 10 and 70% w/v.

6. A process as claimed in claim 1, wherein the vinylbenzene compound is chosen from styrene, -methylstyrene, 4-methoxy styrene and 4-methylstyrene.

7. The process of claim 1 wherein the titanium silicalite the X-ray diffraction spectrum of FIG. 1(b).

8. The process of claim 1 wherein the titanium silicalite has the infrared spectrum of FIG. 1B, FIG. 1C or FIG. 1D.

9. The process of claim 1 wherein the process is carried out in the presence of a polar solvent.

10. A process as claimed in claim 9, wherein the polar solvent is chosen from alcohols, glycols, ketones, ethers and acids, having a number of carbon atoms less than or equal to 6.

11. A process as claimed in claim 10, wherein the alcohol is methanol or tert.butanol.

12. A process as claimed in claim 10, wherein the ketone is acetone.